US012646398B2

(12) United States Patent
Chen et al.

(10) Patent No.: US 12,646,398 B2
(45) Date of Patent: Jun. 2, 2026

(54) ELECTRONIC DEVICE WITH FATIGUE DETECTION FUNCTION

(71) Applicant: GIGA-BYTE TECHNOLOGY CO., LTD., New Taipei City (TW)

(72) Inventors: Kuei-Min Chen, New Taipei City (TW); Tse-Hsien Liao, New Taipei City (TW)

(73) Assignee: GIGA-BYTE TECHNOLOGY CO., LTD., New Taipei City (TW)

( * ) Notice: Subject to any disclaimer, the term of this patent is extended or adjusted under 35 U.S.C. 154(b) by 0 days.

(21) Appl. No.: 18/965,376

(22) Filed: Dec. 2, 2024

(65) Prior Publication Data

US 2025/0356751 A1 Nov. 20, 2025

(30) Foreign Application Priority Data

May 14, 2024 (TW) .................................. 113117665

(51) Int. Cl.
G08B 23/00 (2006.01)
A61B 5/16 (2006.01)
(Continued)

(52) U.S. Cl.
CPC .............. G08B 21/06 (2013.01); A61B 5/163 (2017.08); G06F 3/02 (2013.01); G06V 40/175 (2022.01);
(Continued)

(58) Field of Classification Search
CPC .......... G08B 21/06; A61B 5/163; A61B 5/16; A61B 5/1103; A61B 5/4884;
(Continued)

(56) References Cited

U.S. PATENT DOCUMENTS 5,959,538 A * 9/1999 Schousek ................. G01D 5/16
324/609
2002/0015527 A1 2/2002 Nambu
(Continued)

FOREIGN PATENT DOCUMENTS

CN 101393478 A 3/2009
CN 111556194 A 8/2020
(Continued)

OTHER PUBLICATIONS

Taiwanese Office Action issued in Application No. 113117665, dated Oct. 28, 2024.
Extended European Search Report for European Application No. 25162560.4, dated Apr. 22, 2025.

*Primary Examiner* — Anh V La
(74) *Attorney, Agent, or Firm* — Birch, Stewart, Kolasch & Birch, LLP

(57) ABSTRACT

An electronic device with a fatigue detection function is provided and includes a keyboard, a key detection circuit, a first processing circuit, a control circuit, and a display screen. The keyboard includes at least one key. The key detection circuit detects the pressing state of the key to generate a first detection signal. The first processing circuit converts the first detection signal to a first processing signal. The control circuit determines whether a specific event occurs according to the first processing signal. In response to the specific event, the control circuit sends a reminder signal. The display screen displays a reminder image according to the reminder signal.

17 Claims, 4 Drawing Sheets

400

(51) Int. Cl.

| | |
|---|---|
| *G06F 3/02* | (2006.01) |
| *G06V 40/16* | (2022.01) |
| *G08B 21/06* | (2006.01) |
| *G09G 5/10* | (2006.01) |

(52) U.S. Cl.
CPC ....... *G09G 5/10* (2013.01); *G09G 2320/0626* (2013.01)

(58) Field of Classification Search
CPC . A61B 5/6897; A61B 5/742; A61B 2090/064; G06F 3/02; G06F 3/005; G06V 40/175; G06V 40/168; G06V 40/18; G09G 5/10; G09G 2320/0626
USPC ....... 340/575, 576, 573.1, 573.4, 573.7, 540
See application file for complete search history.

(56) References Cited

U.S. PATENT DOCUMENTS

| | | | |
|---|---|---|---|
| 2013/0176129 A1* | 7/2013 | Li ............................. | A61B 5/18 |
| | | | 340/575 |
| 2013/0260826 A1* | 10/2013 | Nemoto ................ | H04M 1/724 |
| | | | 455/556.1 |
| 2022/0203996 A1* | 6/2022 | Katz ..................... | B60W 50/14 |
| 2023/0063708 A1* | 3/2023 | Gowda ................. | B60W 40/06 |

FOREIGN PATENT DOCUMENTS

| | | |
|---|---|---|
| CN | 111880642 A | 11/2020 |
| CN | 117472316 A | 1/2024 |
| JP | 2007-143913 A | 6/2007 |
| TW | 201505000 A | 2/2015 |

* cited by examiner

ELECTRONIC DEVICE WITH FATIGUE DETECTION FUNCTION

CROSS REFERENCE TO RELATED APPLICATIONS

This Application claims priority of Taiwan Patent Application No. 113117665, filed on May 14, 2024, the entirety of which is incorporated by reference herein.

BACKGROUND OF THE INVENTION

Field of the Invention

The present invention relates to an electronic device, and, in particular, to an electronic device with a fatigue detection function.

Description of the Related Art

The risk of myopia increases the longer a user spends staring at electronic devices. Furthermore, when watching electronic devices for a long time, users may become tired (and may doze off) without realizing it. Additionally, users may accidentally touch keyboards while asleep, which may cause the contents of any open documents to be mistakenly written to or deleted.

BRIEF SUMMARY OF THE INVENTION

In accordance with an embodiment of the disclosure, an electronic device with a fatigue detection function is provided. The electronic device with a fatigue detection function comprises a keyboard, a key detection circuit, a first processing circuit, a control circuit, and a display screen. The keyboard comprises at least one key. The key detection circuit detects the pressing state of the key to generate a first detection signal. The first processing circuit converts the first detection signal to a first processing signal. The control circuit determines whether a specific event occurs according to the first processing signal. In response to the specific event, the control circuit sends a reminder signal. The display screen displays a reminder image according to the reminder signal.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1:
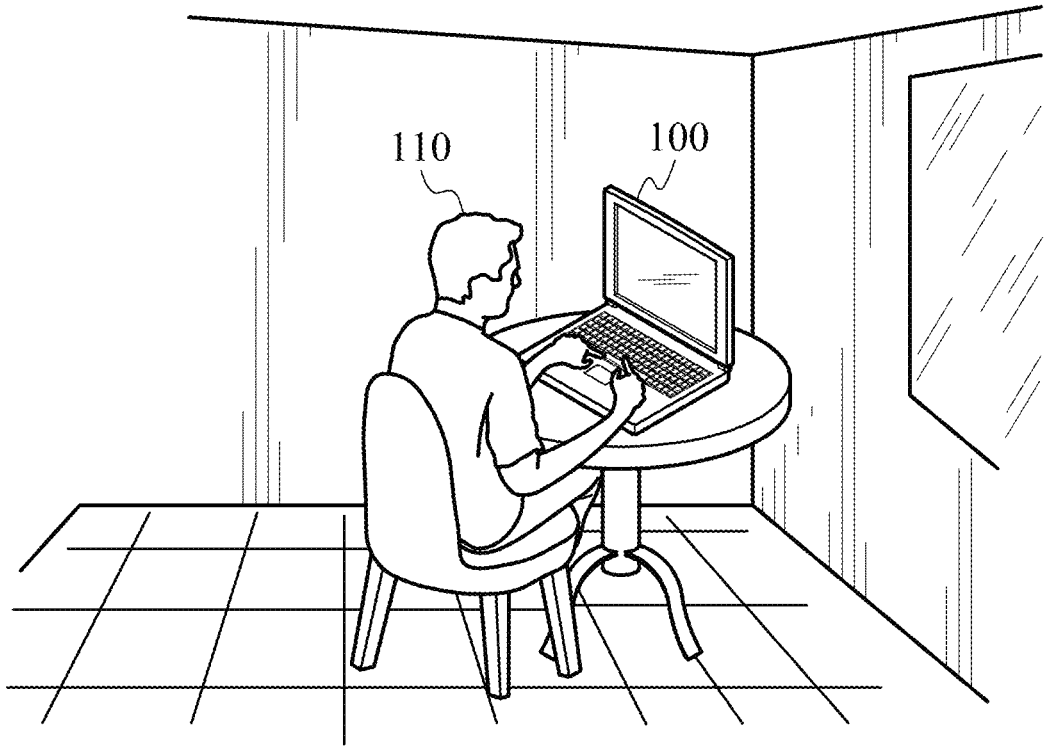
FIG. 1 is a schematic diagram showing an exemplary embodiment of an electronic device.

The present invention will be described with respect to particular embodiments and with reference to certain drawings, but the invention is not limited thereto and is only limited by the claims. The drawings described are only schematic and are non-limiting. In the drawings, the size of some of the elements may be exaggerated for illustrative purposes and not drawn to scale. The dimensions and the relative dimensions do not correspond to actual dimensions in the practice of the invention.

FIG. 1 is a schematic diagram showing an exemplary embodiment of an electronic device. The invention does not limit the type of an electronic device 100. In this embodiment, the electronic device 100 is a laptop computer. The electronic device 100 is equipped with a fatigue detection function. The electronic device 100 detects the behavior of a user 110 to determine whether a fatigue situation occurs in the user 110. When the electronic device 100 detects that the fatigue situation occurs in the user 110, the electronic device 100 presents or displays a reminder image to timely remind the user 110 to stand up and stretch. Additionally, when the user 110 is staring too closely at the electronic device 100 for a long time, the electronic device 100 also reminds the user 110 to take a rest or increase the distance from the electronic device 100.

Figure 2:
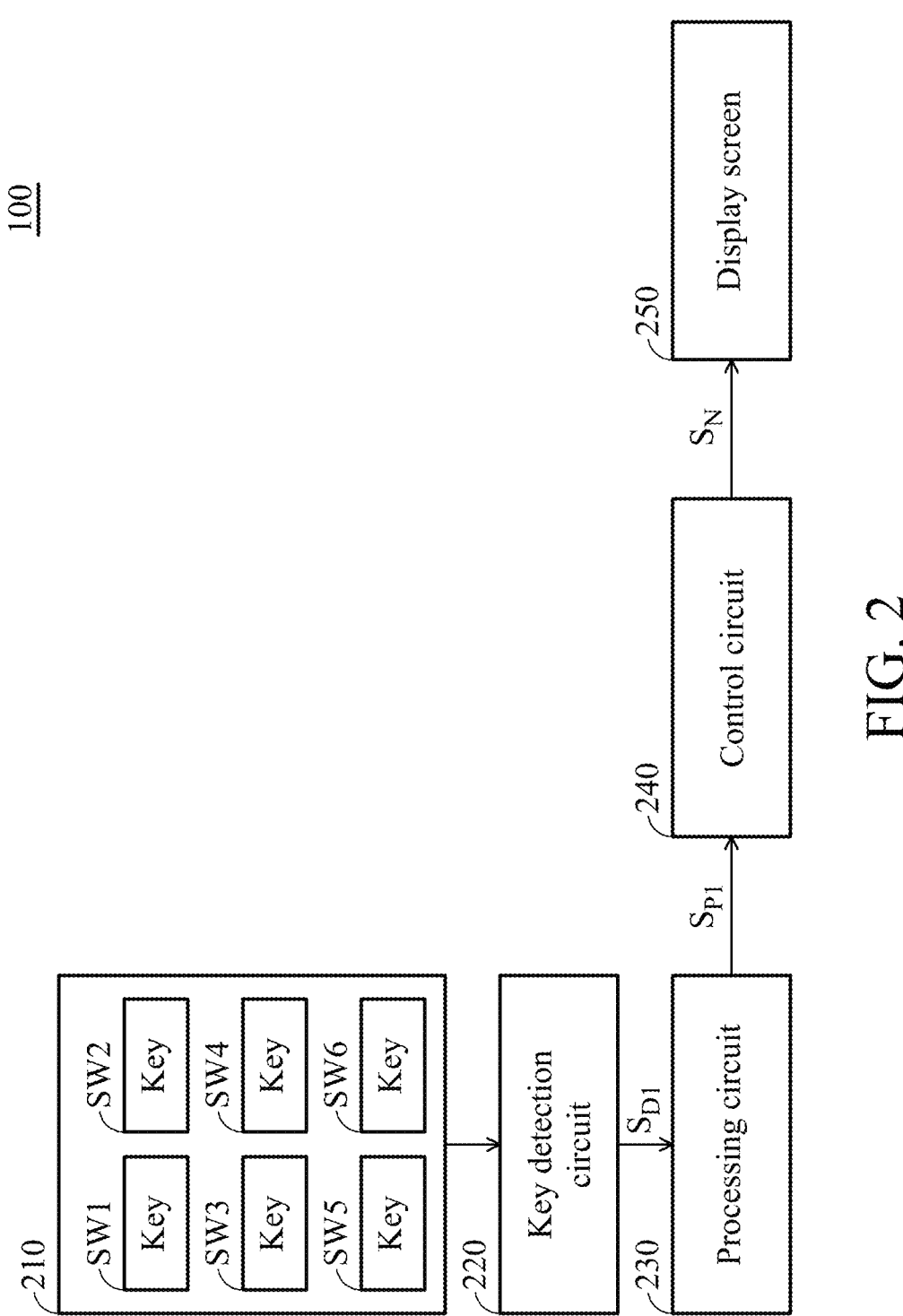
FIG. 2 is a schematic diagram showing an internal structure of one exemplary embodiment of an electronic device.

FIG. 2 is a schematic diagram showing an internal structure of the electronic device 100. For convenience of explanation, FIG. 2 shows only the component circuits related to the present invention without limitation to the present invention. The electronic device 100 may comprise other hardware components or software that controls hardware, which will not be described in detail here. As shown in FIG. 2, the electronic device 100 comprises a keyboard 210, a key detection circuit 220, a processing circuit 230, a control circuit 240, and a display screen 250.

The keyboard 210 comprises at least one key. In this embodiment, FIG. 2 shows keys SW1-SW6, however, the present invention is not limited thereto. In other embodiments, the keyboard 210 may comprise more or fewer keys. In one embodiment, the keyboard 210 is a keyboard of a laptop computer.

Figure 3:
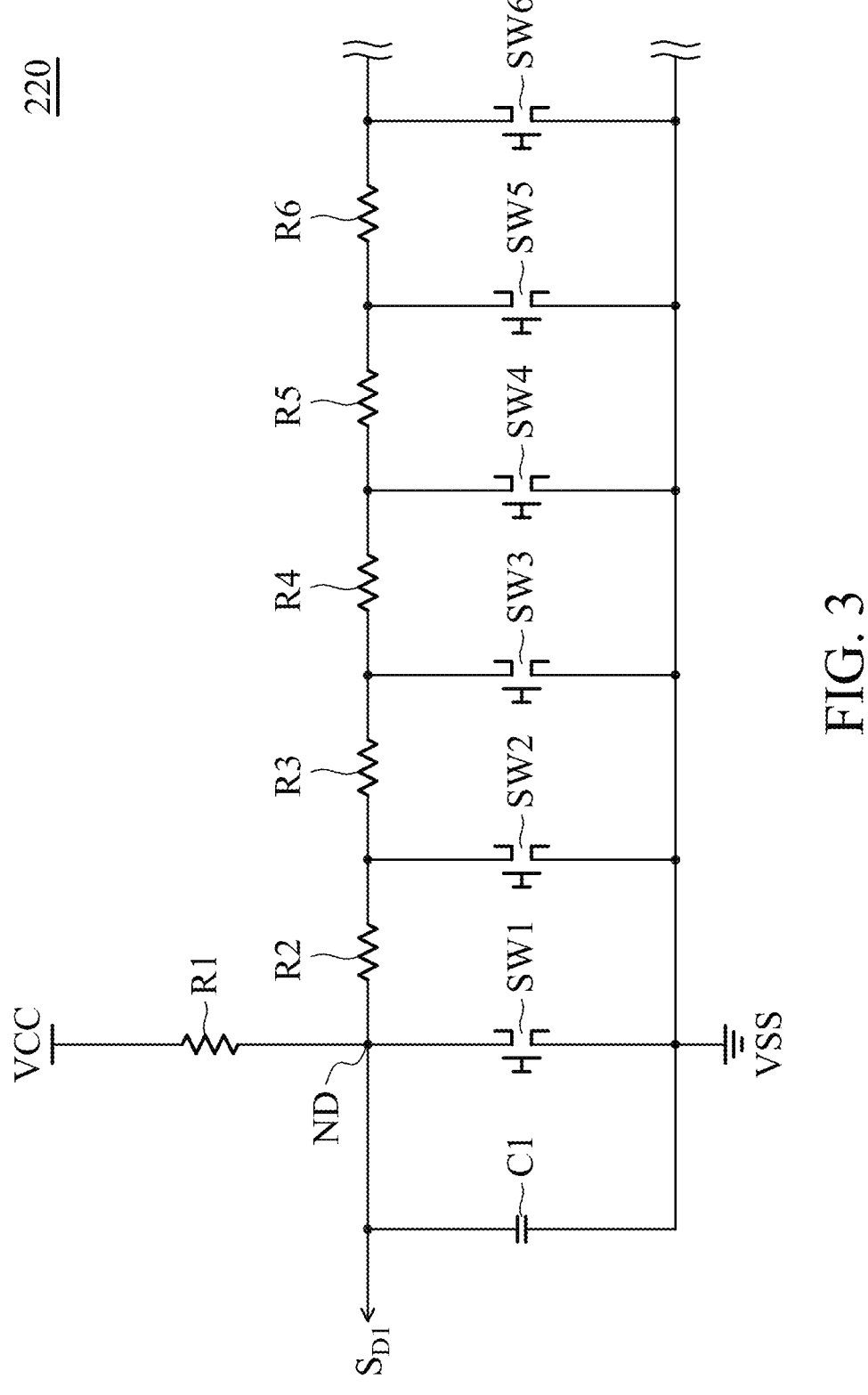
FIG. 3 is a schematic diagram showing an exemplary embodiment of a key detection circuit.

The key detection circuit 220 detects pressing states of the keys SW1-SW6 to generate a detection signal $S_{D1}$. In one embodiment, the key detection circuit 220 detects the pressing states of the keys SW1-SW6 sequentially. FIG. 3 is a schematic diagram showing the key detection circuit 220 of the present invention. The key detection circuit 220 comprises a resistor R1. The resistor R1 is coupled between a power source terminal VCC and a node ND. The key SW1 is coupled between the node ND and a power source terminal VSS. In another embodiment, the key detection circuit 220 further comprises a capacitor C1. The capacitor C1 is coupled between the node ND and the power source terminal VSS.

In other embodiments, the number of resistors of the key detection circuit 220 is related to the number of keys of the keyboard 210. For example, when the keyboard 210 comprises the keys SW1-SW6, the key detection circuit 220 further comprises resistors R2-R6. The resistor R2 is coupled between the node ND and the key SW2. The key SW2 is coupled between the resistor R2 and the power source terminal VSS. The resistor R3 is coupled between the keys SW2 and SW3. The key SW3 is coupled between the resistor R3 and the power source terminal VSS. The resistor R4 is coupled between the keys SW3 and SW4. The key SW4 is coupled between the resistor R4 and the power source terminal VSS. The resistor R5 is coupled between the keys SW4 and SW5. The key SW5 is coupled between the resistor R5 and the power source terminal VSS. The resistor R6 is coupled between the keys SW5 and SW6. The key SW6 is coupled between the resistor R6 and the power source terminal VSS.

Each of the keys SW1-SW6 has an equivalent impedance. When a specific key (such as the key SW1) is pressed with stronger force, the specific key has a smaller equivalent impedance. When a specific key (such as the key SW1) is pressed with lighter force, the specific key has a greater equivalent impedance. Therefore, according to the voltage level of the node ND, whether the keys SW1-SW6 are pressed and the force with which the keys SW1-SW6 are pressed can be detected or determined. In this embodiment, the voltage level of the node ND serves as the detection signal $S_{D1}$.

Referring to FIG. 2, the processing circuit 230 converts the detection signal $S_{D1}$ to generate a processing signal $S_{P1}$. In one embodiment, the processing circuit 230 is an analog-to-digital conversion (ADC) circuit. In this embodiment, the analog-to-digital conversion circuit converts the voltage of the node ND from an analog format to a digital format, and the converted result is taken as the processing signal $S_{P1}$.

The control circuit 240 determines whether a specific event occurs according to the processing signal $S_{P1}$. The case where the specific event occurs indicates that a fatigue situation has occurred in the user 110. Therefore, the control circuit 240 sends a reminder signal $S_N$. The present invention does not intend to limit the structure of the control circuit 240. In one embodiment, the control circuit 240 comprises an embedded controller (EC).

The control circuit 240 determines the force with which each of the keys SW1-SW6 is pressed according to the processing signal $S_{P1}$. When the force with which one of the keys SW1-SW6 is pressed does not meet a first predetermined condition, the control circuit 240 determines that the specific event occurs. Therefore, the control circuit 240 sends the reminder signal $S_N$. In another embodiment, the control circuit 240 determines the frequency at which each of the keys SW1-SW6 is pressed according to the processing signal $S_{P1}$. When the frequency at which one of the keys SW1-SW6 is pressed does not meet a second predetermined condition, the control circuit 240 determines that the specific event occurs. Therefore, the control circuit 240 sends the reminder signal $S_N$.

In other embodiments, the control circuit 240 determines the time when each of the keys SW1-SW6 is pressed continuously according to the processing signal $S_{P1}$. When the time when one of the keys SW1-SW6 is pressed continuously is longer than a first predetermined time, the control circuit 240 sends the reminder signal $S_N$. In this embodiment, the case where the time when one of the keys SW1-SW6 is pressed continuously is longer the first predetermined time indicates that the user 100 may fall asleep due to excessive fatigue and press on a certain key with a finger. Therefore, the control circuit 240 may enter a sleep mode after sending the reminder signal $S_N$.

In some embodiments, the control circuit 240 first collects the processing signal $S_{P1}$ within a preset period (such as 1 hour or 1 minute), calculates the processing signal $S_{P1}$, and then takes the calculation result as the first or second predetermined condition. For example, the control circuit 240 first collects the processing signal $S_{P1}$ within one hour to determine the average value of the force with which the user 110 presses the key(s) of the keyboard 210 in one minute, such as a value in a range of 700-1000, and the takes the average value of the force as the first predetermined condition. In this case, when one of the keys SW1-SW6 is pressed with a force value that does not fall within the range of 700-1000 (for example, the force value is less than 400), the control circuit 240 sends the reminder signal $S_N$. In addition, the case where one of the keys SW1-SW6 is pressed with a force value that suddenly changes to the value of 1000 or 0 indicates that the user 110 may have fallen asleep while pressing one of the keys SW1-SW6, or that the user 110 may have fallen asleep without using the keyboard 210. Therefore, the control circuit 240 automatically enters the sleep mode to achieve the power saving function.

In another embodiment, the control circuit 240 calculates the frequency at which the user 110 presses the keys of the keyboard 240 according to the processing signal $S_{P1}$, and uses the calculation result as the second predetermined condition. For example, according to the processing $S_{P1}$, the control circuit 240 determines that the average frequency at which the user 110 presses the keys per minute is 60 times (that is, the second predetermined condition). In this case, when the frequency at which the user 110 presses the keys is lower than ⅓ of the average frequency (for example, 20 times), the control circuit 240 sends the reminder signal $S_N$.

The display screen 250 displays or shows a reminder screen according to the reminder signal $S_N$ to remind the user 110 of whether taking a rest is needed. In one embodiment, the control circuit 240 uses the WMI manner and cooperates with the BIOS and EC to directly pop up a reminder message on the display screen 250 under the OS. In another embodiment, the control circuit 240 triggers a specific application program (APP) to remind the user 110 of whether a fatigue situation occurs and whether taking a rest is needed. In some embodiments, the specific application program also informs the user 110 of the current usage status of the electronic device 100, such as the temperature of the GPU and the fan speed. The user 110 can also adjust the fan speed or the color of the LED light on the housing of the electronic device 100 through a specific application program.

Figure 4:
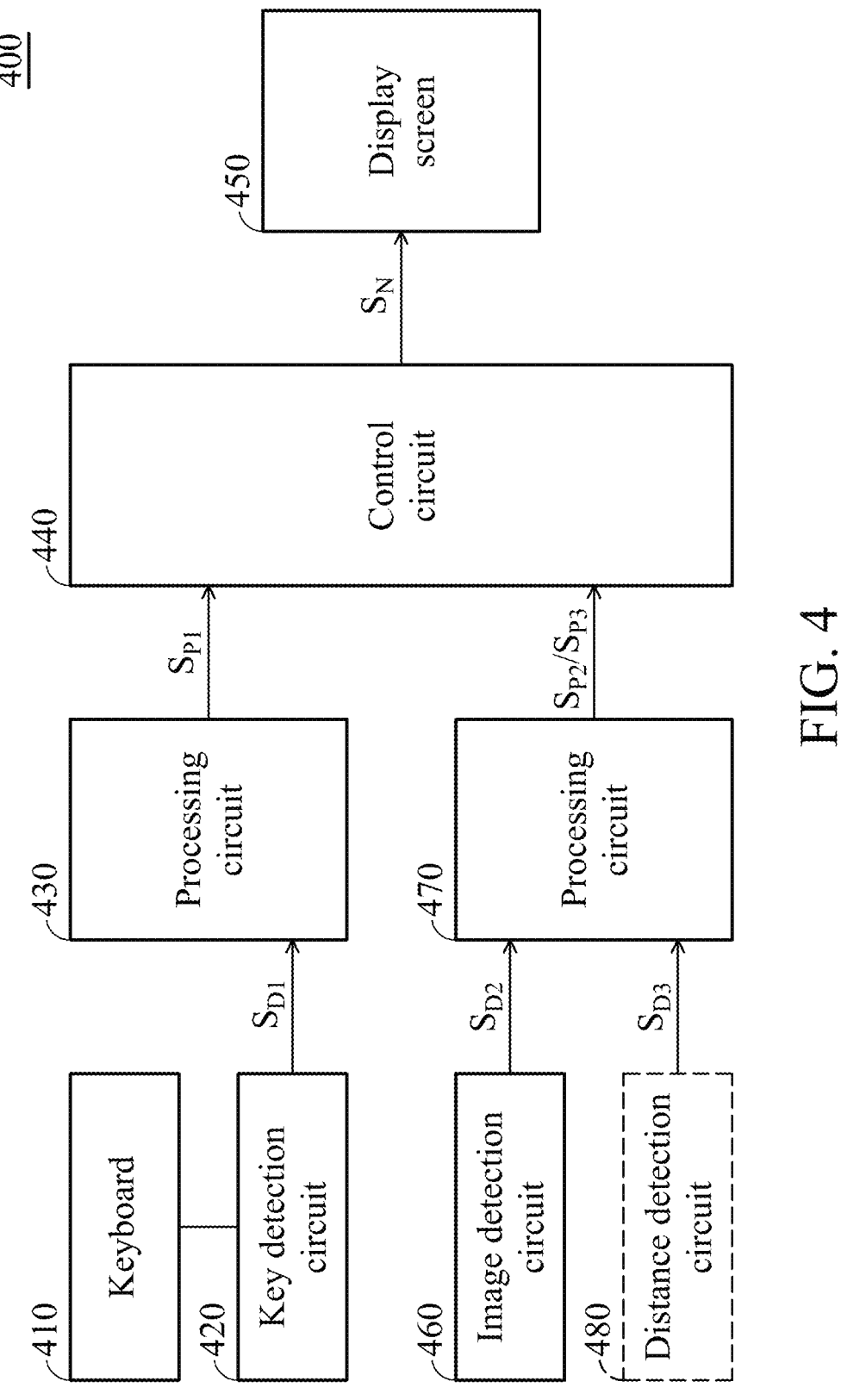
FIG. 4 is a schematic diagram showing an internal structure of another exemplary embodiment of an electronic device.

FIG. 4 is a schematic diagram showing an internal structure of another exemplary embodiment of an electronic device. As shown in FIG. 4, an electronic device 400 comprises a keyboard 410, a key detection circuit 420, processing circuits 430 and 470, a control circuit 440, a display screen 450, and an image detection circuit 460. Since the features of the keyboard 410, the key detection circuit 420, the processing circuit 430, and the display screen 450 are similar to the those of the keyboard 210, the key detection circuit 220, the processing circuit 230, and the display screen 250 in FIG. 2, the related description is omitted here.

In this embodiment, the image detection circuit 460 detects a user's face to generate a detection signal $S_{D2}$. The present invention does not intend to limit the structure of the image detection circuit 460. In one embodiment, the image detection circuit 460 comprises a lens (not shown). The lens may be fixed on the housing of the electronic device 400.

The processing circuit 470 processes the detection signal $S_{D2}$ through a first algorithm to generate a processing signal $S_{P2}$. In one embodiment, the processing circuit 470 takes the detection signal $S_{D2}$ into the first algorithm to analyze changes in the user's eyes, the user's mouth, or both.

The control circuit 440 determines whether a specific event occurs according to the processing signals $S_{P1}$ and $S_{P2}$. In one embodiment, the control circuit 440 determines the force with which the keys of the keyboard 410 are pressed and the frequency at which the keys are pressed according to the processing signal $S_{P1}$. In other embodiments, according to the processing signal $S_{P2}$, the control circuit 440 determines the frequency at which the user blinks their eyes and the frequency at which the period that the user's mouth is open exceeds a predetermined time (for example, 1 second).

For example, when the force with which the keys of the keyboard 410 are pressed does not meet the first predetermined condition (for example, the force value with which one key is pressed does not fall within the range of 700-1000) and the frequency at which the user blinks their eyes does not fall within a first normal range (for example, 1217 times per minute), it is determined that the specific event (the fatigue situation of the user) has occurred. Therefore, the control circuit 440 sends a reminder signal $S_N$ to remind the user to take a rest. In another embodiment, when the frequency at which the keys of the keyboard 410 are pressed (for example, 60-80 times per minute) does not meet the second predetermined condition and the frequency at which the user blinks their eyes does not fall within the first normal range, the control circuit 440 sends the reminder signal $S_N$.

In other embodiments, when the force with which the keys of the keyboard 410 are pressed does not meet the first predetermined condition and the frequency at which the period that the user's mouth is open exceeds the predetermined time (for example, 1 second) increases, the control circuit 440 sends the reminder signal $S_N$. In some embodiments, when the frequency at which the keys of the keyboard 410 are pressed does not meet the second predetermined condition and when the frequency at which the period that the user's mouth is open exceeds the predetermined time increases, the control circuit 440 sends the reminder signal $S_N$.

As described above, the control circuit 440 determines whether the user is experiencing fatigue symptoms according to the force and frequency at which the user presses the keys of the keyboard 410, and further determines whether the frequency at which the user blinks their eyes increases or the frequency at which the period that the user's mouth is open exceeds 1 second increases according to the processing signal $S_{P2}$. Thus, the accuracy of determining whether the fatigue situation occurs in the user can be increased, and the occurrence of erroneous determination can be reduced. In some embodiments, the control circuit 440 records the duration of the user using the electronic device 400 according to the processing signal $S_{P2}$. In this case, when the duration of the user using the electronic device 400 is excessive long, the control circuit 440 may remind the user through the display screen 450 that the user should stand up and stretch. In some embodiments, the display screen 450 displays or shows the time the user continuously uses the electronic device 400 for the reference.

In one embodiment, the electronic device 400 further comprises a distance detection circuit 480. The distance detection circuit 480 detects whether an object is close to the display screen 450 and generates a detection signal $S_{D3}$ according to the detection result. In this embodiment, the processing circuit 470 processes the detection signal $S_{D3}$ through a second algorithm to generate a processing signal $S_{P3}$. The processing circuit 470 takes the detection signal $S_{D3}$ into the second algorithm to analyze the distance between the object and the display screen 450. In some embodiments, the image detection circuit 460 and the distance detection circuit 480 operate simultaneously.

The control circuit 440 determines whether the specific event occurs according to the processing signals $S_{P1}$-$S_{P3}$. For example, the control circuit 440 determines the force with which the keys of the keyboard 410 are pressed or the frequency at which the keys of the keyboard 410 are pressed according to the processing signal $S_{P1}$. In another embodiment, the control circuit 440 determines the frequency at which the user blinks their eyes or the frequency at which the period of the user's mouth being open exceeds the predetermined time according to the processing signal $S_{P2}$. In other embodiments, when the control circuit 440 determines that the user is located in front of the display screen 450 according to the processing signal $S_{P2}$, it indicates that the object detected by the distance detection circuit 480 is the user's face. Therefore, the control circuit 440 determines whether the distance between the user and the display screen 450 is appropriate according to the processing signal $S_{P3}$. However, when the control circuit 440 determines that the user is not in front of the display screen 450 according to the processing signal $S_{P2}$, it indicates that the object detected by the distance detection circuit 480 is not the user's face. Therefore, the control circuit 440 ignores the processing signal $S_{P3}$ to avoid erroneously sending the reminder signal $S_N$.

When the control circuit 440 determines that the user is in front of the display screen 450 according to the processing signal $S_{P2}$, the control circuit 440 determines whether the specific events occurs according to the processing signals $S_{P1}$-$S_{P3}$. For example, when the force with which the keys of the keyboard 410 are pressed does not meet the first predetermined condition, the frequency at which the user blinks their eyes does not fall within the first normal range, and the distance, which is detected by the distance detection circuit 480, between the object (that is, the user) and the display screen 450 does not fall within a second normal range (for example, being greater than 45 cm), the control circuit 440 sends the reminder signal $S_N$. The display screen 450 displays or shows the reminder screen according to the reminder signal $S_N$. The reminder screen may remind the user to take a rest or to keep a proper distance to the display screen 450, thereby avoiding eye discomfort.

In another embodiment, when the frequency at the keys of the keyboard 410 are pressed does not meet the second predetermined condition, the frequency at which the user blinks their eyes does not fall within the first normal range, and the distance, which is detected by the distance detection circuit 480, between the object (that is, the user) and the display screen 450 does not fall within the second normal range, the control circuit 440 sends the reminder signal $S_N$.

In other embodiments, when the force with which the keys of the keyboard 410 are pressed does not meet the first predetermined condition, the frequency at which the period of the user's mouth opening exceeds the predetermined time increases, and the distance, which is detected by the distance detection circuit 480, between the object (that is, the user) and the display screen 450 does not fall within the second normal range, the control circuit 440 sends the reminder signal $S_N$. In some embodiments, when the frequency at the keys of the keyboard 410 are pressed does not meet the second predetermined condition, the frequency at which the period of the user's mouth opening exceeds the predetermined time increases, and the distance, which is detected by the distance detection circuit 480, between the object (that is, the user) and the display screen 450 does not fall within the second normal range, the control circuit 440 sends the reminder signal $S_N$.

In this embodiment, the control circuit 440 determines whether the user is experiencing fatigue symptoms according to the force and frequency at which the user presses the keys of the keyboard 410, further determines whether the frequency at which the user blinks their eyes increases or the frequency at which the period of the user's mouth is open exceeds 1 second increases according to the processing signal $S_{P2}$, and also determines the distance, which is detected by the distance detection circuit 480, between the object and the display screen 450 decreases according to the processing signal $S_{P3}$. Thus, the accuracy of determining whether the fatigue situation occurs in the user can be increased, and the occurrence of erroneous determination can be reduced. In some embodiments, when the distance, which is detected by the distance detection circuit 480, between the object (for example, the user) and the display screen 450 constantly changes, it indicates that the user may be dozing off. Therefore, the control circuit 440 may gradually reduce the brightness of the display screen 450 to achieve the power saving function.

In one embodiment, the control circuit 440 defines the first predetermined condition according to the processing signal $S_{P1}$. For example, during a preset period (such as 1 hour), the control circuit 440 collects the processing signal $S_{P1}$ to calculate the average value of the force with which the user presses the keys of the keyboard 410 in one minute, such as a value in a range of 700-1000. In this case, the control circuit 440 takes the distribution interval of the average value of the force (700-1000) as the first predetermined condition. In other embodiments, the control circuit 440 calculates the strength of the force with which the user presses the keys of the keyboard 410 per minute and compares it with the calculated strength of the force in the next minute. When the force with which the user presses the keys of the keyboard 410 suddenly drops below the value of 400, or the value suddenly changes to the value of 1000 or 0, it indicates that the user has fallen asleep while pressing the keys of the keyboard 410. Therefore, the control circuit 440 sends the reminder signal $S_N$.

In another embodiment, the control circuit 440 defines the first normal range according to the processing signal $S_{P2}$. For example, during a preset period (for example, 1 hour), the control circuit 440 collects the processing signal $S_{P2}$ to calculate the frequency at which the user blinks their eyes in one minute. In this case, the control circuit 440 takes the distribution interval of the user's average blinking frequency per minute as the first normal range. In other embodiments, the control circuit 440 compares the blinking frequency of the current minute with the blinking frequency of the next minute. If the blinking frequency of the current minute exceeds ⅓ times the blinking frequency of the previous minute, it indicates that the fatigue situation occurs in the user. In one embodiment, when the control circuit 440 determines that the number of times the user opens the mouth for more than 1 second increases according to the processing signal $S_{P2}$, it indicates that the user is experiencing fatigue symptoms. Therefore, the control circuit 440 determines whether the force with which or the frequency at which the user presses the keys of the keyboard 410 is abnormal according to the processing signal $S_{P1}$. When the force with which or the frequency at which the user presses the keys of the keyboard 410 does not meet the first predetermined condition, the control circuit 440 sends the reminder signal $S_N$.

In other embodiments, the control circuit 440 defines the second normal range according to the processing signal $S_{P3}$. For example, when the control circuit 440 determines that the user is located in front of the display screen 450 according to the processing signal $S_{P2}$, the control circuit 440 collects the processing signal $S_{P3}$ during a preset period (for example, 1 hour) to calculate the distance between the user and the image detection circuit 460 which is, for example, more than 45 cm. In this case, the control circuit 440 takes the normal distance between the user and the image detection circuit 460 as the second normal range.

In some embodiments, when a specific events occurs, it indicates that the user may have fallen asleep. Therefore, the control circuit 440 may gradually reduce the brightness of the display screen 450. In this case, when the specific event has not been resolved, the control circuit 440 may require other circuits of the electronic device 400 to enter the sleep mode. However, when the specific event is resolved, the control circuit 440 restores the brightness of the display screen 450.

It will be understood that when an element or layer is referred to as being "coupled to" another element or layer, it can be directly coupled to the other element or layer or intervening elements or layers may be present. In contrast, when an element or layer is referred to as be "directly coupled to" another element or layer, there are no intervening elements or layers present.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. It will be understood that although the terms "first," "second," etc. may be used herein to describe various elements, these elements should not be limited by these terms. These terms are only used to distinguish one element from another. In the following claims, the terms "first," "second," etc. are used merely as labels, and are not intended to impose numerical requirements on their objects.

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An electronic device with a fatigue detection function, comprising:

a keyboard comprising at least one key;

a key detection circuit detecting a pressing state of the key to generate a first detection signal;

a first processing circuit converting the first detection signal to a first processing signal;

a control circuit determining whether a specific event occurs according to the first processing signal, wherein in response to the specific event occurring, the control circuit sends a reminder signal;

a display screen displaying a reminder image according to the reminder signal;

an image detection circuit detecting a face of a user to generate a second detection signal;

a second processing circuit processing the second detection signal through a first algorithm to generate a second processing signal; and a distance detection circuit detecting whether an object is close to the display screen to generate a third detection signal, wherein:

the first algorithm is applied to analyze changes in the user's eyes, the user's mouth, or both, the second processing circuit processes the third detection signal through a second algorithm to generate a third processing signal;

the control circuit determines whether the specific event occurs according to the first, second, and third processing signals.

2. The electronic device with the fatigue detection function as claimed in claim 1, wherein the key detection circuit comprises:

a resistor coupled between a first power source terminal and a node, wherein:

the key is coupled between the node and a second power source terminal; and the first processing circuit is an analog-to-digital conversion circuit, and the analog-to-digital conversion circuit converts a voltage of the node to generate the first detection signal.

3. The electronic device with the fatigue detection function as claimed in claim 1, wherein the control circuit determines force with which the key is pressed according to the first processing signal, and in response to the force with which the key is pressed not meeting a first predetermined condition, the control circuit sends the reminder signal.

4. The electronic device with the fatigue detection function as claimed in claim 1, wherein the control circuit determines a frequency at which the key is pressed according to the first processing signal, and in response to the frequency at which the key is pressed not meeting a second predetermined condition, the control circuit sends the reminder signal.

5. The electronic device with the fatigue detection function as claimed in claim 4, wherein the control circuit determines a time during which the key is pressed continuously according to the first processing signal, and in response to the time during which the key is pressed continuously being longer than a first predetermined time, the control circuit enters a sleep mode after sending the reminder signal.

6. The electronic device with the fatigue detection function as claimed in claim 1, wherein:

the control circuit determines force with which the key is pressed according to the first processing signal;

the control circuit determines a frequency at which the user blinks the eyes according to the second processing signal; and in response to the force with which the key is pressed not meeting a first predetermined condition and the frequency at which the user blinks the eyes not falling within a first normal range, the control circuit sends the reminder signal.

7. The electronic device with the fatigue detection function as claimed in claim 1, wherein:

the control circuit determines a frequency at which the key is pressed according to the first processing signal;

the control circuit determines a frequency at which the user blinks the eyes according to the second processing signal; and in response to the frequency at which the key is pressed not meeting a second predetermined condition and the frequency at which the user blinks the eyes not falling within a first normal range, the control circuit sends the reminder signal.

8. The electronic device with the fatigue detection function as claimed in claim 1, wherein:

the control circuit determines force with which the key is pressed according to the first processing signal;

the control circuit determines a frequency at which a period that the mouth of the user is open exceeds a second predetermined time according to the second processing signal; and in response to the force with which the key is pressed not meeting a first predetermined condition and the frequency at which the period that the user's mouth is open exceeds the second predetermined time increasing, the control circuit sends the reminder signal.

9. The electronic device with the fatigue detection function as claimed in claim 1, wherein:

the control circuit determines a frequency at which the key is pressed according to the first processing signal;

the control circuit determines a frequency at which a period that the mouth of the user is open exceeds a second predetermined time according to the second processing signal; and in response to the frequency at which the key is pressed not meeting a second predetermined condition and the frequency at which the period that the user's mouth is open exceeds the second predetermined time increasing, the control circuit sends the reminder signal.

10. The electronic device with the fatigue detection function as claimed in claim 1, wherein the second algorithm is applied to analyze a distance between the object and the display screen.

11. The electronic device with the fatigue detection function as claimed in claim 10, wherein:

the control circuit determines force with which the key is pressed according to the first processing signal;

the control circuit determines a frequency at which the user blinks the eyes according to the second processing signal;

the control circuit determines the distance between the object and the display screen according to the third processing signal; and in response to the force with which the key is pressed not meeting a first predetermined condition, the frequency at which the user blinks the eyes not falling within a first normal range, and the distance between the object and the display screen not falling within a second normal range, the control circuit sends the reminder signal.

12. The electronic device with the fatigue detection function as claimed in claim 11, wherein the control circuit defines the first predetermined condition according to the first processing signal, defines the first normal range according to the second processing signal, and defines the second normal range according to the third processing signal.

13. The electronic device with the fatigue detection function as claimed in claim 10, wherein:

the control circuit determines a frequency at which the key is pressed according to the first processing signal;

the control circuit determines a frequency at which the user blinks the eyes according to the second processing signal;

the control circuit determines the distance between the object and the display screen according to the third processing signal; and in response to the frequency at which the key is pressed not meeting a second predetermined condition, the frequency at which the user blinks the eyes not falling within a first normal range, and the distance between the object and the display screen not falling within a second normal range, the control circuit sends the reminder signal.

14. The electronic device with the fatigue detection function as claimed in claim 13, wherein the control circuit defines the second predetermined condition according to the first processing signal, defines the first normal range according to the second processing signal, and defines the second normal range according to the third processing signal.

15. The electronic device with the fatigue detection function as claimed in claim 10, wherein:

the control circuit determines force with which the key is pressed according to the first processing signal;

the control circuit determines a frequency at which a period that the mouth of the user is open exceeds a second predetermined time according to the second processing signal;

the control circuit determines the distance between the object and the display screen according to the third processing signal; and in response to the force with which the key is pressed not meeting a first predetermined condition, the frequency at which the period that the mouth of the user is open exceeds the second predetermined time increasing, and the distance between the object and the display screen not falling within a second normal range, the control circuit sends the reminder signal.

16. The electronic device with the fatigue detection function as claimed in claim 10, wherein:

the control circuit determines a frequency at which the key is pressed according to the first processing signal;

the control circuit determines a frequency at which the period that the mouth of the user is open exceeds a second predetermined time according to the second processing signal;

the control circuit determines the distance between the object and the display screen according to the third processing signal; and in response to the frequency at which the key is pressed not meeting a second predetermined condition, the frequency at which the period that the mouth of the user is open exceeds the second predetermined time increasing, and the distance between the object and the display screen not falling within a second normal range, the control circuit sends the reminder signal.

17. The electronic device with the fatigue detection function as claimed in claim 1, wherein in response to the specific event occurring, the control circuit reduces brightness of the display screen, and in response to the specific event being resolved, the control circuit restores the brightness of the display screen.

* * * * *